United States Patent [19]

Keil

[11] Patent Number: 5,686,076
[45] Date of Patent: Nov. 11, 1997

[54] GD-NEGATIVE BOVINE HERPESVIRUS MUTANT, CAPABLE OF DIRECT CELL-TO-CELL TRANSMISSION

[75] Inventor: Günther Keil, Tübingen, Germany

[73] Assignee: Akzo Nobel N.V., Arnhem, Netherlands

[21] Appl. No.: 503,781

[22] Filed: Jul. 18, 1995

[30] Foreign Application Priority Data

Jul. 18, 1994 [EP] European Pat. Off. ............. 94202081

[51] Int. Cl.$^6$ .............................. C12N 7/00; C12N 7/01; C12N 15/38; A61K 39/295
[52] U.S. Cl. .................... 424/199.1; 424/202.1; 424/229.1; 435/235.1; 536/23.72
[58] Field of Search ............................ 424/199.1, 202.1, 424/229.1; 536/23.72; 435/235.1

[56] References Cited

FOREIGN PATENT DOCUMENTS

WO 94/01573  1/1994  WIPO .
WO 94/63595  2/1994  WIPO .

OTHER PUBLICATIONS

F. Fehler et al., *Journal of Virology*, 66:2:831–839, Feb. 1992.

S.K. Tikoo et al., *Journal of Virology*, 64:10:5132–5142, Oct. 1990.

Mettenlater et al 1994 J. Gen. Virol vol. 75:1723–1733.

Ligas et al 1988 J. Virol 62(5) 1486–1494.

*Primary Examiner*—Mary E. Mosher
*Assistant Examiner*—Ali R. Salimi
*Attorney, Agent, or Firm*—Mary E. Gormley; William M. Blackstone

[57] ABSTRACT

The present invention relates to a gD-negative Bovine Herpesvirus mutant, that has the property of direct cell-to-cell transmission. The invention also relates to a DNA-fragment capable of conferring this property to Bovine Herpesviruses, not possessing the direct cell-to-cell transmission capability. Also, the invention relates to a vaccine based on this mutant, and a method for the protection of animals against Bovine Herpesvirus.

10 Claims, 3 Drawing Sheets

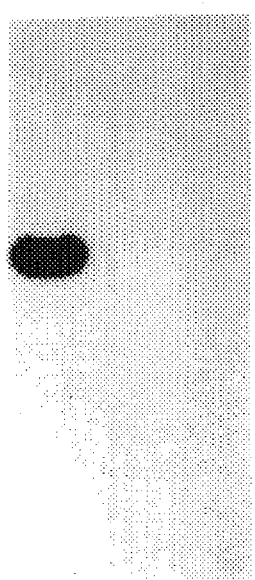
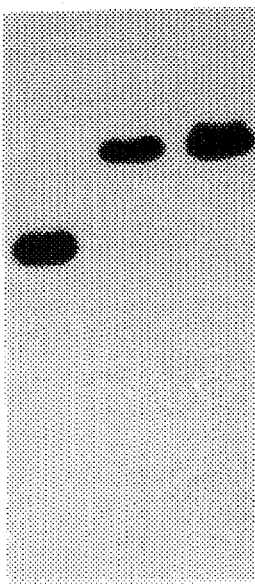
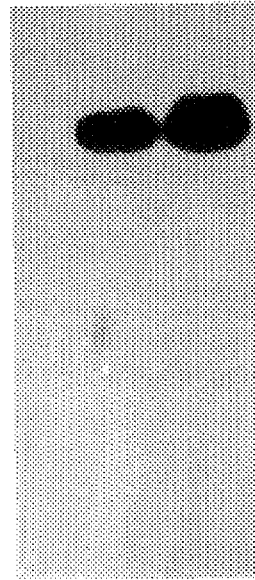
gD
FIG. 2A
gI
FIG. 2B
lacZ
FIG. 2C
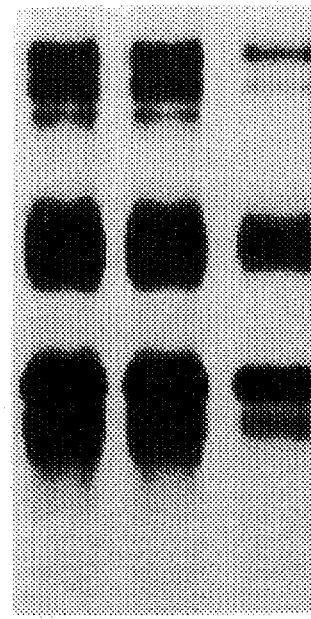
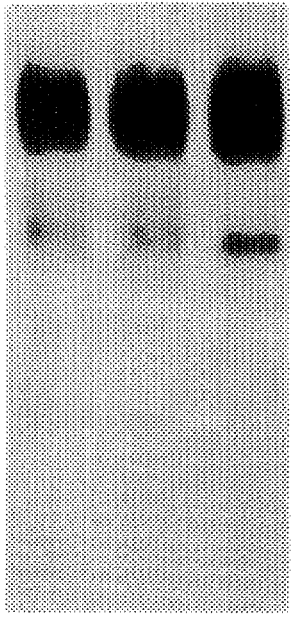
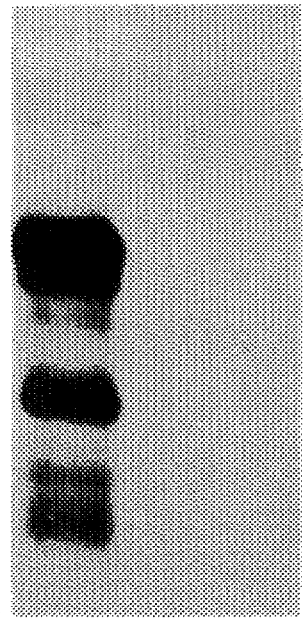
gB
FIG. 3A
gC
FIG. 3B
gD
FIG. 3C

GD-NEGATIVE BOVINE HERPESVIRUS MUTANT, CAPABLE OF DIRECT CELL-TO-CELL TRANSMISSION

The present invention relates to a gD-negative Bovine Herpesvirus mutant, that displays the property of direct cell-to-cell transmission, a DNA-fragment capable of conferring this property to Bovine Herpesviruses lacking the property of direct cell-to-cell transmission, a vaccine based on this mutant, and a method for the protection of animals against Bovine Herpesvirus.

BACKGROUND OF THE INVENTION

The herpesviruses are a widespread family of large viruses containing double-stranded DNA, causing disease in mammals, birds, reptiles, fish and amphibians.

The double-stranded DNA codes for about 30–35 polypeptides, depending on the genus. The molecular weight of the DNA greatly varies between 120 kbp in Channel Cat Fish Herpesvirus to 230 kbp in Humin Cytomegalovirus. The GC-content of the DNA varies even more; from 32% in Dog Herpesvirus to 72–73% in Bovine Herpesvirus.

The viral agents causing Infectious Bovine Rhinotracheitis (IBR), Infectious Pustular Vulvovaginitis (IPV) and Infectious Balanoposthitis (IBP) belong to the Herpesviruses, more specifically to the sub-family Alphaherpes Viridae (Roizman, B. In Fields, B. N., Knipe, D. M. (ed.) Fundamental Virology. Ravens Press, N.Y.: 841–847 (1991)).

They are all designated Bovine Herpesvirus I (Roizman et al.; *Intervirology* 16: 210–217 (1981)), and more recently Bovid Herpesvirus I (Ludwig, H. in B. Roizman (Ed.) The Herpesviruses. Plenum Press N.Y., vol. 2:135–214 (1983)). In cross-neutralisation tests BHV-I isolates all exhibit only one serotype, regardless their origin from IBR or IPV/IBP cases (Gillespie et al.; Cornell Vet. 49:288–297 (1959), McKercher et al.; Can. J. Comp. Med. 23:320–328 (1959)). Restriction enzyme analysis of large numbers of different isolates has revealed differences in restriction site patterns, but no correlation exists between the patterns and the origin of the isolates. Therefore it is now generally accepted that the site of infection with BHV-I determines the effects of the disease, whereas the causative agent is in all cases the Bovine Herpesvirus I.

Currently, within the sub-family Alphaherpesvirinae several different Bovine Herpesvirus types are known: type I (mentioned above), II (Bovine Mammilitis virus), IV (Bovine cytomegalovirus) and V (Bovine Encephalitis virus).

Transmission of infectious Bovine Rhinotracheitis can occur for instance a) by animals that are acutely infected with or without showing clinical signs, and that are still shedding virus, and b) by animals that are latently infected and start shedding recurrent virus after stress.

Spread of IPV/IBP occurs e.g. by contaminated semen, natural service, the teaser bull, or by the herdsmen.

The most common manifestation of BHV-I infection is bovine rhinotracheitis which varies from a mild respiratory disease to a severe infection of the entire respiratory tract.

From an economical point of view, IBR is also the most dramatic manifestation of BHV-I infection.

Another relatively important form of BHV-I infection is the genital form, leading to pustular vulvovaginitis in cows and, comparatively, to infectious balanoposthitis in bulls.

Although seen less frequently, the virus is also associated with abortion, conjunctivitis and encephalitis.

BHV-I is widely spread among cattle in all continents, but its host range is limited. Many wild species have been found seropositive, but distinct clinical signs have only been observed in cattle.

Although IBR and IPV have been known in Europe for more than a century, it appears that wild ruminants in Africa and in zoos are the true reservoir of the virus.

Morbidity rates in both IBR and IPV are usually 100% provided that the animals are in close contact (for IPV).

If morbidity is <100% then the animals are protected by antibodies. Fatalities are rare however, in the case of IBR and IPV. In young calves, however, death as a result of BHV-I induced encephalitis is common. Next to this, several strains of BHV-I have shown to induce abortion.

Due to secondary bacterial infections, pneumoniae and enteritis may occur (Bielefeld-Ohmann et al.; J. Infect. Diseases 151:937–947 (1985))

Immunity against Herpesviruses is dependent on at least two mechanisms: a) the induction of neutralising antibodies and complement-dependent lysis for the inactivation of free virus, and b) the induction of cytotoxic T-cells for the elimination of virus-infected cells.

Generally speaking, cattle can be protected against infection by pathogenic micro-organisms and viruses, e.g. Bovine Herpesvirus with live vaccines, inactivated vaccines and subunit vaccines.

However these types of vaccines may suffer from a number of drawbacks. The use of attenuated vaccines always carries the risk of inoculation of animals with inadequately attenuated pathogenic microorganisms. In addition, the attenuated microorganisms may revert to a virulent state resulting in disease of the inoculated animals and, consequently, spread of the pathogens to other animals. Moreover, a problem with combined live viral vaccines is the mutual influence of the antigenic components resulting in a decrease of potency of one or more of the components.

Inactivated vaccines are generally considered safe, but they generally induce only a low level of immunity, requiring repeated immunizations. Furthermore, the neutralisation inducing antigenic determinants of the pathogens may become altered by the inactivation treatment, decreasing the immunising potency of the vaccine. In addition, cellular immunity is to a lesser extend triggered by inactivated vaccines.

Subunit vaccines have the same drawbacks as inactivated vaccines, and additionally, their spectrum of protection is smaller since they contain less different antigenic determinants than the whole organism.

In recent years, recombinant DNA technology has offered the opportunity to develop safer live mutants. This has been done by deliberate inactivation of those genes that play a role in virulence.

These recombinant DNA-derived modified live viruses can be used not only for the preparation of a vaccine against Bovine Herpesvirus, they can also be used as a carrier for foreign genetic information coding for antigenic determinants of other infectious diseases of cattle. This obviates any potential risk associated with the use of attenuated vaccines based on these other infectious diseases of cattle. This kind of modified live carrier vaccine stimulates both the cellular and humoral immune system in a potent way without the explicit need of an adjuvant and offers the possibility of a multivalent vaccine without the risk of adverse mutual interference of different antigenic components.

Even though the above mentioned new generation of recombinant carrier vaccines is generally considered safe with regard to their virulence, there still are several arguments against their use:

a) genetically modified live vaccines and carrier vaccines are safe in normal immuno-competent hosts. This is however not the case in immuno-compromised hosts; they may suffer from severe illness due to infection with even an attenuated pathogen. The solution to this problem might seem to be simply not to vaccinate immuno-compromised animals. Selective vaccination however is not possible: since the live vaccine virus is shed by vaccinated animals, it can infect all animals in the vicinity of the vaccinated animals, including immuno-compromised animals.

b) In addition to a), it is well known that viruses only moderately pathogenic for one species, may be lethal to other species. A striking example is the pseudorabies virus, also a member of the alphaherpesvirus subfamily of the Herpesviridae. This virus is moderately pathogenic for grown-up pigs, whereas it is absolutely lethal for e.g. cats, dogs, horses and sheep.

This means that a modified live pseudorabies vaccine virus, shed by pigs, may still be very pathogenic for other animal species, e.g. farm animals living in the environment of these pigs.

c) The use of recombinant carrier viruses may cause modifications in the cell or tissue tropism of the virus, i.e. the type of cell or tissue that is (are) infected. This is depending on the nature of the foreign gene(s) that is (are) incorporated in the genome of the carrier. The interaction between viral proteins and host cell receptors determines the cell or tissue tropism of the virus. Therefore, if a virus carries foreign proteins in its membrane, as may be the case with recombinant carrier viruses, this might alter the cell or tissue tropism of the virus. This change in tropism is not restricted to cells or tissues within one host; it may also lead to a change in host tropism.

d) there is a strong reluctance on both political, ethical and partially scientific grounds, to allow the use of recombinant microorganisms and viruses in the field.

For one of the alpha-herpesviridae, pseudorabies virus (PRV), the above-mentioned problems have been solved as follows: recombinant pseudorabies viruses have been constructed that possess the beneficial features of live modified carrier viruses, but are unable to shed after infection (WO 94/01573, WO 94/03595).

Shedding refers to the release of progeny virus from the animal into the environment. This may happen through the excrements, but also through milk, or during slaughtering.

The construction of such a non-shedding virus became possible since it was discovered which genes are involved in the process of infection. In the case of PRV, the so-called gp50 gene was known to be essential for the infection of cells. Therefore, gp50-negative viruses are no longer infectious. (Petrovskis et al; J. Virol. 59:216–223 (1986)

A recombinant cell line was made, in which the gene coding for PRV gp50 is expressed. This cell line was transfected with DNA of gp50-negative PRV. Progeny virus, excreted by the cell line appeared to be infectious, due to the fact that gp50 is present on the envelop of the virus. Genetically however, the progeny virus is still gp50-negative.

Infection of the host animal with this type of virus will therefore lead to infection of a number of cells, and expression in those cells of the genetic information of PRV and possibly additional foreign genetic information, carried by the (recombinant carrier) PRV.

It is however impossible for the progeny virus grown in the host animal to infect any other cell, since the genetic information for gp50, that is essential for infection, is lacking.

See Rauh, I. and Mettenleiter, T. C. (J. Virol 65:5348–5356 (1991)) and Peeters et al. (J. Virol 66:894–905 91992)).

At the same time it was clear that gp50 is not necessary for direct cell-to-cell transmission. See Rauh, and also Peeters, and see Heffner et al, J. Virol 67:1529–1537 (1993). This implicates that once a cell is infected by a phenotypically gp50-completed virus, this virus spreads from this cell by direct cell-to-cell transmission. This process does not need the presence of gp50.

As a result, a large number of cells surrounding the primarily infected cells will be expressing genetic information from PRV and additional foreign gene(s) carried by PRV.

This phenomenon is very important, since it is the only way to express enough antigenic material to trigger the immune system. Without this process of direct cell-to-cell transmission in the absence of gp50, a physiologically unacceptable high doses of virus particles has to be administered in order to obtain immunity.

Several herpesviruses other than PRV have genes that are to a certain degree homologous to the gp50 gene of PRV. Such homologs have been described for the gD-gene of Equine Herpesvirus (Flowers et al, Virology 180; 175–184 (1991), the gD-gene of Herpes Simplexvirus (Ligas et al, J. Virol. 62; 1486–1494 (1988)) and the gD-gene of Bovine Herpesvirus type I (Tikoo et al, J. Virol. 64; 5132–5142 (1990), Fehler et al., J. Virol. 66: 831–839(1992)).

It is clear from these papers that the pseudorabies gp50-gene product is exceptional in that it is not essential for direct cell-to-cell transmission.

Both the gD-gene of Herpes Simplex Virus and of Bovine Herpesvirus I are absolutely essential not only for infectivity (as is the case with PRV) but also for direct cell-to-cell transmission. (See Ligas (HSV) and see Fehler (BHV)).

Thus, a Bovine Herpesvirus gD-negative mutant does not display direct cell-to-cell transmission. Therefore, the approach followed for PRV, to construct a non-infectious vaccine virus by deleting gp50, that nevertheless is capable of direct cell-to-cell transmission, and by doing so, is capable of producing sufficient levels of antigens, is not feasible for Bovine Herpesvirus.

Surprisingly it has now been found that a gD-negative Bovine Herpesvirus mutant could be obtained that displays the property of direct cell-to-cell transmission. This mutant will also be referred to as the ctcs$^+$ mutant.

SUMMARY OF THE INVENTION

A gD-negative bovine herpesvirus mutant that differs from standard gD-negative bovine herpesvirus by being capable of direct cell-to-cell transmission. Due to the fact that this mutant possesses direct cell-to-cell transmission, its genetic information becomes expressed in large numbers of cells, surrounding each primarily infected cell, in spite of the fact that the virus is not infectious. Thus, the number of virus particles administered to the host is kept within a pharmaceutically acceptable level, while at the same time, a sufficiently high antigen level is reached to trigger an immune response.

It is obvious, that all Bovine Herpesvirus types, comprising a gD-gene can be used for the construction of a Bovine herpesvirus that is displaying the property of direct cell-to-cell transmission, according to the present invention.

In a preferred form of the invention, a gD-negative Bovine Herpesvirus type I mutant is used.

BRIEF DESCRIPTION OF THE DRAWINGS

FIG. 2 illustrates the hybridization of DNA from wtBHV-1 (lanes 1), gD-lacZ$^+$-BHV (lanes 2) and gD-lacZ$^+$ ctcs$^+$BHV-1 (lanes 3) after cleavage with HindIII, size separation on agarose gel and transfer to nitrocellulose, with a gD-specific probe (a), a gI-specific probe (b) and a lacZ-specific probe (c).

FIG. 3 illustrates polyacrylamide-gel electrophoresis on immunoprecipitated proteins from $^{35}$S-labeled cells, infected with wtBHV-1 (lanes 1), gD-lacZ$^+$BHV-1 (lanes 2) and gD-lacZ$^+$ctcs$^+$BHV-1 (lanes 3) after incubation with anti-gB antibodies (a), anti-gC antibodies (b) and anti gD-antibodies (c).

FIG. 4 FIG. 4B shows plaque formation (dark cells) by the gD-negative BHV-1 ctcs$^+$ mutant according to the invention.

FIGS. 4A and 4C show co-cultivation of gD-complementing (4A) and non-complementing (4C) cells with supernatant and killed cells obtained from 4B.

FIGS. 4E shows co-cultivation of non-complementing cells and living cell progeny of the cell culture seen on 4B, comprising the gD-negative BHV-1 ctcs$^+$ mutant according to the invention.

FIGS. 4D and 4F show co-cultivation of gD-complementing (4D) and non-complimenting (4F) cells and living cells from 4E.

DETAILED DESCRIPTION OF THE INVENTION

The gD-negative Bovine herpesvirus mutant according to the present invention is obtainable by co-transfection of DNA of a gD-negative Bovine Herpesvirus and a DNA containing an 8.5 kbp HindIII-BglII restriction fragment, which DNA is isolatable from *E. coli* transformed with this DNA and deposited with the Collection Nationale de Cultures de Microorganismes (CNCM) of the Institut Pasteur, 25, Rue du Docteur Roux, 75724 Paris CEDEX 15 at Paris France, under nr. I-1446.

Figure 1:
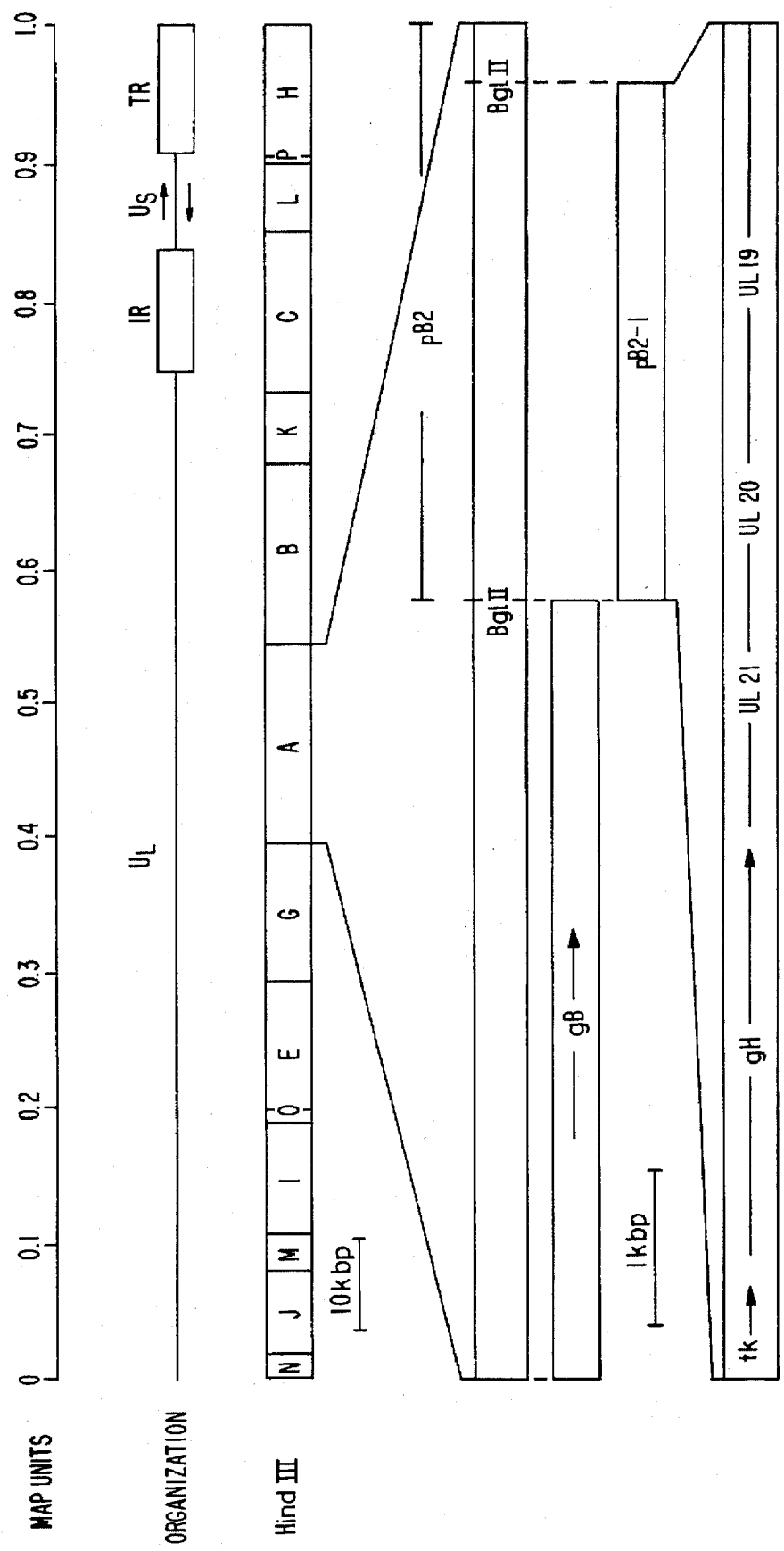
FIG. 1 shows the location of the genomic map of BHV.

The above mentioned HindIII-BglII fragment comprises a gH-gene with a mutation. This mutated gH-gene provides the surprising character of the mutant of the present invention. The location of the gH-gene is indicated in FIG. 1.

It is obvious that all sub-fragments of the said 8.5 kbp HindIII-BglII restriction fragment, that are capable of conferring the property of direct cell-to-cell transmission, are also part of the invention.

After co-transfection of a suitable host cell, homologous recombination yields the Bovine Herpesvirus mutant according to the invention. This mutant can easily be selected for, since (contrary to standard gD-negative Bovine herpesvirus) it is plaque-forming, due to its capability of direct cell-to-cell transmission.

It goes without saying that it is also possible to first perform co-transfection with wild-type Bovine Herpesvirus I and the DNA containing the 8.5 kbp HindIII-BglII restriction fragment, followed by modification of the gD-gene in order to obtain a gD-negative mutant.

The present invention also refers to Bovine Herpesvirus mutants that are complemented with gD. As mentioned above, any gD-negative Bovine alpha-Herpesvirus mutant is non-infectious, regardless its capability of direct cell-to-cell transmission.

For vaccination purposes, however, it would be highly desirable to have a mutant that is capable of only one single infection cycle. In order to make the mutant according to the present invention infective, it suffices to transfect DNA of the mutant virus on cells complementing for gD. In such cells, progeny virus is phenotypically complemented for gD, and thus is infective. Such gD-complementing cells have been described by Fehler et al (J. Virol. 66:831–839 (1992)). Virus isolated from the supernatant of these cells is phenotypically gD-positive but genotypically gD-negative, and therefore capable of infecting host cells for only one single infective cycle.

Alternatively, live gD-negative Bovine Herpesviruses can be used for the preparation of a vaccine according to the invention without the need of propagation on a complementing cell line if the vaccine comprises said herpesviruses in a cell-associated form, e.g. as a suspension of infected cells.

It is possible to maintain a replicating cell line containing a replicative form of the virus, in the absence of gD. Mixing cells of this cell line with virus-free cells of the same or a compatible cell line leads by cell-cell contact to infection of all the cells in the culture, thus providing a means of concomitantly propagating viruses and virus-containing cells that are both phenotypically and genotypically free of gD-homolog.

It goes without saying that Bovine Herpesviruses according to the present invention may have additional deletions, insertions, point mutations or other genomic alterations. These alterations may, for example, be deletions of the Thymidine Kinase gene, the glycoprotein gI-gene or the glycoprotein gE-gene.

It is possible, by means of recombinant DNA technology, to insert foreign genetic information (heterologous DNA) into the genome of the gD-negative Bovine Herpesvirus mutant according to the present invention, and by doing so, to use BHV as a carrier virus for this information.

It is one of the objectives of the present invention to provide a recombinant carrier virus.

Therefore, preferably the BHV mutant according to the present invention comprises an insertion with a heterologous DNA sequence.

If the inserted gene is provided with the appropriate sequences for expression, the inserted genetic information will be expressed together with the genetic information of the virus.

Thus, in an more preferred form, in the BHV mutant according to the present invention, the heterologous DNA sequence is under the control of a promotor regulating the expression of said heterologous DNA sequence in a cell infected with said BHV mutant.

In a most preferred form, the heterologous DNA sequence encodes an antigen of a bovine pathogen.

This antigen is advantageously derived from the group consisting of Bovine Rotavirus, Bovine Viral Diarrhoea virus, Parainfluenza type 3 virus, Bovine Paramyxovirus, Foot and Mouth Disease virus, Bovine Coronavirus, Bovine Respiratory Syncytial virus and Pasteurella haemolytica.

The present invention also concerns a vaccine for the protection of cattle against Bovine Herpesvirus infection, comprising a gD-negative Bovine Herpesvirus mutant according to the present invention.

Preferentially, this vaccine comprises a virus according to the present invention, additionally comprising genetic information for an antigen of another bovine pathogen.

For the preparation of a live vaccine the BHV mutant according to the present invention can be grown on susceptible cells.

Growth can, for example, be performed on a cell culture of bovine origin. This cell culture may be a gD-complementing cell culture.

The viruses thus grown can be harvested by collecting the tissue or cell culture fluids and/or cells. The live vaccine may be prepared in the form of a suspension or may be lyophilized.

In addition to an immunogenically effective amount of the recombinant BHV-I the vaccine may contain a pharmaceutically acceptable carrier or diluent.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of BAYOL F® or MARCOL52®, saponins or vitamin-E solubilisate).

The present invention also provides a method for the protection of animals against Bovine Herpesvirus mutants, which comprises administering a vaccine according to the present invention to said animals.

It is clear that in case the vaccine comprises a virus according to the present invention, additionally comprising genetic information for an antigen of another bovine pathogen, the above-mentioned method also provides protection against said another bovine pathogen.

For administration to animals, the BHV mutant according to the present invention can be given inter alia intranasally, intradermally, subcutaneously or intramuscularly.

The useful effective amount to be administered will vary depending on the age, weight, mode of administration and type of pathogen against which vaccination is sought. A suitable dosage can be for example about $10^3$–$10^7$ pfu/animal.

A BHV mutant according to the invention can also be used to prepare an inactivated vaccine.

The present invention also relates to an 8.5 kbp HindIII-BglII restriction fragment, said fragment being isolatable from $E.\ coli$ transformed with DNA comprising said fragment, and deposited with the Collection Nationale de Cultures de Micro-organismes (CNCM) of the Institut Pasteur at Paris France under nr. I-1446.

EXAMPLE 1

Cell- and virus growth conditions

For the propagation of virus, Madin-Darby bovine kidney cells (MDBK) were used. For the propagation of (non-direct cell-to-cell transmissible) gD-negative mutants, a complementing cell line according to Fehler (Fehler et al., J. Virol. 66: 831–839 (1992)) was used. In this cell line, also of MDBK-origine, the BHV-1 gene for gD is inserted and constitutively expressed.

The gD-negative BHV-1 mutant carrying the lacZ-gene instead of the gD-gene was also made by Fehler (vide supra), according to standard molecular biological techniques.

Cells were grown in Dulbecco's minimal essential medium (DMEM) supplemented with 5% fetal calf serum, penicillin (100 U/ml), streptomycin (100 µg/ml, and L-glutamine (0.35 mg/ml).

Viruses were propagated on these cells according to standard methods.

Construction of gD-negative BHV-1 mutant with $ctcs^+$-characteristics:

BHV-1 viruses possessing the specific $ctcs^+$-character are obtained by co-transfection of suitable host cells with BHV-1 virus DNA and a specific 8.5 kbp HindIII-BglII restriction fragment. This specific fragment can be isolated from $E.\ coli$ transformed with this fragment and deposited with the Collection Nationale de Cultures de Micro-organismes (CNCM) of the Institut Pasteur at Paris France under nr. I-1446.

Suitable host cells are, for example, MDBK-cells.

Co-transfection of the DNAs is done according to standard techniques, as described, for example, in Maniatis (Maniatis, T. et al, in "Molecular cloning; a laboratory manual, (1982) ISBN 0-87969-136-0).

If the viral DNA is isolated from a gD-lacZ$^+$BHV-1 mutant, screening for recombinant viruses with the $ctcs^+$ characteristics must be done in the presence of X-gal, the chromogenic substrate for the lacZ gene product.

Cells harbouring recombinant viruses are then easily recognised by their ability to form large blue plaques after three or more days. (Contrary to transformed cells containing non-recombined viruses that are only found as single blue cells).

Hybridization experiments

In order to prove that the $ctcs^+$ mutant according to the present invention is indeed gD-negative, the following hybridization experiments were done:

DNA from wtBHV-1, gD$^-$lacZ$^+$-BHV-1 and gD$^-$lacZ$^+$ctcs$^+$BHV-1 was digested with HindIII, and separated on agarose gels. Separation was followed by transfer to nitrocellulose. The nitrocellulose filters were subsequently hybridized with a gD-specific probe, a gI-specific probe, and a lacZ-specific probe.

The wtBHV-1 DNA was obtained from wild-type BHV-1 virus, whereas gD$^-$lacZ$^+$-BHV-1 DNA was obtained from a gD-negative BHV-1 mutant in which the gD-gene had been replaced by the lacZ-gene. The gD$^-$lacZ$^+$ctcs$^+$BHV-1 DNA was obtained from the gD-negative BHV-1 mutant with the direct cell-to-cell transmission property according to the invention.

Results: from lanes 1, 2 and 3 in FIG. 2a (hybridized with a gD-specific probe), it is clear that only the wild-type BHV-1 virus (lane 1) has the gD-gene. Neither the gD$^-$lacZ$^+$-BHV-1 DNA nor the gD$^-$lacZ$^+$ctcs$^+$BHV-1 DNA have the gD-gene or a fragment thereof.

This shows that the surprising direct cell-to-cell transmission property cannot be attributed to the gD gene.

In FIG. 2b, the same DNAs were hybridized with gI-DNA, a gene that is present in all three DNAs. This experiment shows that the lack of hybridization in lanes a2 and a3 is not due to the fact that no DNA was present in these lanes, but indeed to the lack of the gD-gene.

In FIG. 2c, the same DNAs were hybridized with lacZ-DNA. The result of this experiment shows that both gD$^-$lacZ$^+$-BHV-1 DNA and gD$^-$lacZ$^+$ctcs$^+$BHV-1 DNA have still retained their lacZ$^+$ character, as was expected.

Immunoprecipitation experiments

In addition to the DNA-hybridization test, an immunological test was done to check for the gD-negative character of both the gD$^-$lacZ$^-$BHV-1 virus and gD$^-$lacZ$^+$ctcs$^+$BHV-1 virus.

PAGE-gels of immunoprecipitated proteins from $^{35}S$-labeled cells, infected with BHV-1 (see FIG. 3, lanes 1), $gD^-lacZ^+$BHV-1 (lanes 2) and $gD^-lacZ^+ctcs^+$BHV-1 (lanes 3) were made and blotted. These blots were used in immunological assays, using anti-gB (blot a), anti-gC (blot b) and anti-gD (blot c) monoclonal antibodies.

Results: antibodies against gB and gC are reactive in all blots, but antibodies against gD are only reactive in lane 1, which contains the wtBHV-1. These results confirm the results of the hybridization experiment.

Confirmation of direct cell-to-cell transmission properties

Figure 4:
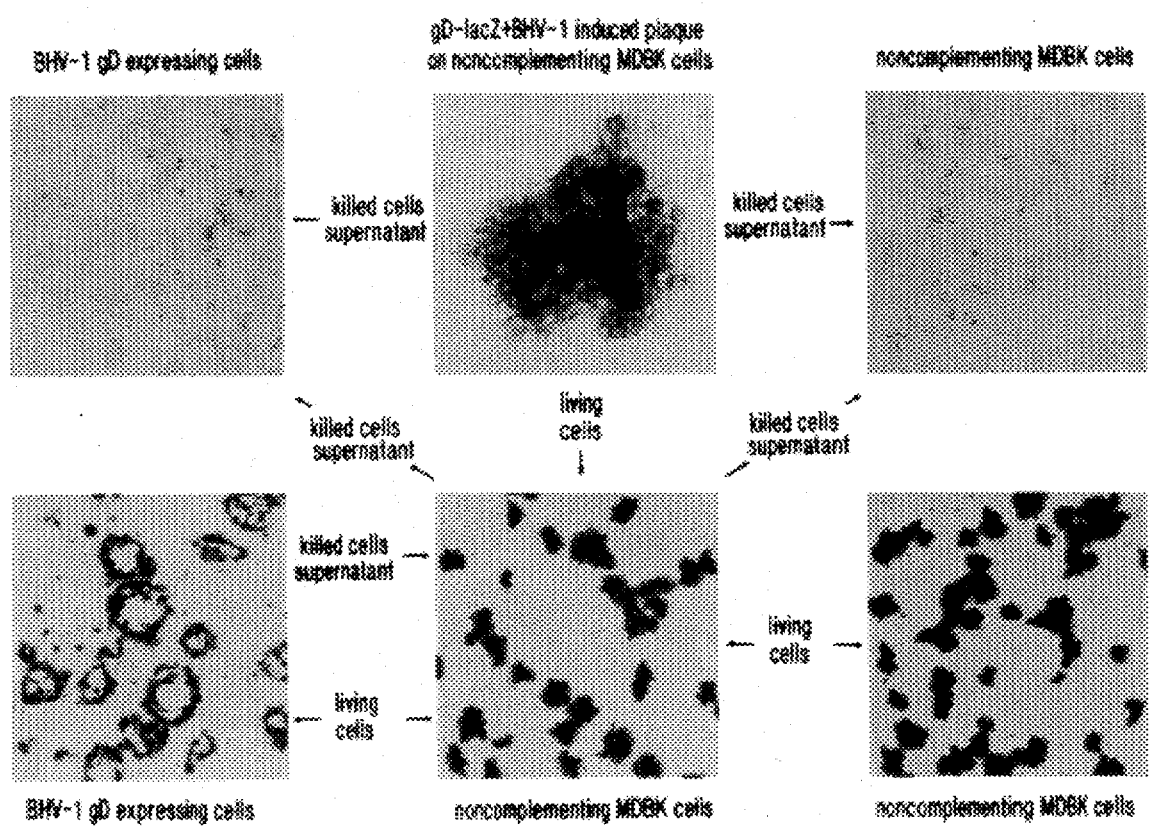

In order to check if the gD-negative Bovine Herpesvirus mutant according to the present invention was indeed capable of direct cell-to-cell transmission, the following experiments were done:

a) supernatant and killed cells (killed by freeze/thawing followed by sonication) from a culture comprising the direct cell-to-cell transmission ($ctcs^+$) mutant were co-cultured with gD-complementing cells and with non-complementing cells (see FIG. 4). FIG. 4B shows plaque formation (dark cells) by the gD-negative BHV-1 $ctcs^+$ mutant according to the invention. FIGS. 4A and 4C show co-cultivation of gD-complementing and non-complementing cells with supernatant and killed cells from FIG. 4B.

Results: in neither the gD-complementing cells nor the non-complementing cells, any plaque-formation can be seen. Killed cells can no longer participate in direct cell-to-cell transmission of the virus. The supernatant, that contains free virus particles from lysed cells, also does not cause plaque formation since the virus particles are not infectious due to lack of gD.

Therefore, this experiment proves that direct cell-to-cell transmission is the means of transmission of the gD-negative $ctcs^+$ mutant according to the present invention.

b) living cells from a culture comprising the direct cell-to-cell transmission ($ctcs^+$) mutant according to the invention were co-cultured with non-complementing cells.

To this end, a suspension of cells from the picture in FIG. 4B was made and seeded upon a culture of non-complementing cells.

Results: FIG. 4E shows the results of this co-cultivation: living cells spread over the layer of non-complementing cells have, due to direct cell-to-cell transmission, induced plaque-formation in the non-complementing cells. This proves that indeed cells comprising the $ctcs^+$ mutant according to the invention are capable of cofferring plaque-formation due to the direct cell-to-cell transmission character of the mutant.

c) living cells from plaques of FIG. 4E (described under b) were co-cultured with gD-complementing cells and with non-complementing cells.

Results: FIG. 4D shows that co-cultivation of gD-complementing cells and living cell progeny comprising the $ctcs^+$ mutant (FIG. 4E) leads to the formation of large plaques. This is a result of the fact that from complementing cells that obtained the $ctcs^+$ mutant through direct cell-to-cell transmission, two processes occur: direct cell-to-cell transmission from these cells to neighbouring cells and release of infectious particles that in turn can infect other cells.

The FIG. 4F picture shows co-cultivation of non-complementing cells and living cell progeny comprising the $ctcs^+$ mutant (FIG. 4E). As expected, again new plaques are formed as a result of direct cell-to-cell transmission.

EXAMPLE 2

Animal experiments on safety, virulence and efficacy of the gD-negative Bovine Herpesvirus mutant according to the present invention.

Animal experiments were started to test for safety, low virulence and high efficacy, and lack of shedding of the gD-negative mutant.

The gD-negative mutant was compared with wild-type BHV and pathogenic effects were compared with non-infected animals.

Two different virus titers were given, i.e. 5.3 $^{10}log\ TCID_{50}$ and 4.0 $^{10}log\ TCID_{50}$. Viruses were given as indicated in the table below:

| Group | Animal No. | Vaccine | Dose | Route |
|---|---|---|---|---|
| One | 1 to 4 | BHV wild-type | 5.3 $^{10}log\ TCID_{50}$ | Intranasal |
| Two | 5 to 8 | BHV wild-type | 5.3 $^{10}log\ TCID_{50}$ | Intramuscular |
| Three | 9 to 12 | BHV GD-mutant | 5.3 $^{10}log\ TCID_{50}$ | Various* |
| Four | 13 to 16 | None (control) | | |
| Five | 17 to 20 | BHV wild-type | 4.0 $^{10}log\ TCID_{50}$ | Intranasal |
| Six | 21 to 24 | BHV wild-type | 4.0 $^{10}log\ TCID_{50}$ | Intramuscular |
| Seven | 25 to 28 | BHV GD-mutant | 4.0 $^{10}log\ TCID_{50}$ | Various* |

*2 mls by each of the following routes: intranasal, intramuscular and intravenous.

I claim:

1. A Bovine Herpesvirus (BHV) mutant that is gD-negative and contains a mutated gH gene, wherein said BHV mutant is capable of direct cell-to-cell transmission, and wherein said mutated gH gene is present in an 6.5 kbp HindIII-BglII restriction fragment, or a subfragment thereof, said fragment being obtainable from the *E. coli* deposited with the CNCM under accession No. I-1446.

2. The BHV mutant according to claim 1, which is a type I serotype.

3. The BHV mutant according to claim 1, obtainable by co-transfection of DNA of a gD-negative Bovine Herpesvirus and a DNA containing an 8.5 kbp HindIII-BglII restriction fragment, or a subfragment thereof, said subfragment being capable of conferring the property of direct cell-to-cell transmission, said DNA being isolatable from *E. coli* transformed with said DNA, and deposited with the Collection Nationale de Cultures de Micro-organismes (CNCM) of the Institut Pasteur at Paris France under nr. I-1446.

4. The BHV mutant according to claim 1, wherein the Herpesvirus mutant is complemented with gD.

5. The BHV mutant according to claim 1, wherein the mutant comprises an insertion with a heterologous DNA sequence.

6. A vaccine for the protection of cattle against BHV infection, comprising a BHV mutant according to claim 1.

7. The vaccine according to claim 6, wherein said BHV mutant further comprises at least one heterologous DNA sequence that expresses an antigen of a different bovine pathogen.

8. The vaccine of claim 7, wherein said antigen is selected from the group consisting of antigens of Bovine Rotavirus, Bovine Viral Diarrhoea virus, Parainfluenza type 3 virus, Bovine Paramyoxovirus, Foot and Mouth Disease virus, Bovine coronavirus, Bovine Respiratory Syncytial virus and *Pasteurella haemolytica*.

9. A method for the protection of animals against Bovine Herpesvirus infection, which comprises administering an immunogenically effective amount of a vaccine according to claim 6.

10. An 8.5 kbp HindIII-BglII restriction fragment, said fragment being isolatable from *E. coli* transformed with DNA comprising said fragment, and deposited with the Collection Nationale de Cultures de Micro-organismes (CNCM) of the Institut Pasteur at Paris France under nr. I-1446.

* * * * *